United States Patent [19]

Bernhardt et al.

[11] Patent Number: 5,117,027

[45] Date of Patent: May 26, 1992

[54] PROCESS FOR THE PREPARATION OF ORGANOSILANES CONTAINING METHACRYLOYLOXY OR ACRYLOYLOXY GROUPS

[75] Inventors: Günther Bernhardt, St. Augustin; Klaus-Dieter Steffen, Hennef; Margret Haas, Köln; Heinz Kragl, Troisdorf, all of Fed. Rep. of Germany

[73] Assignee: Hüls Aktiengesellschaft, Marl. Fed. Rep. of Germany

[21] Appl. No.: 777,149

[22] Filed: Oct. 16, 1991

[30] Foreign Application Priority Data

Oct. 31, 1990 [DE] Fed. Rep. of Germany ....... 4034612

[51] Int. Cl.$^5$ ............................................. C07F 7/08
[52] U.S. Cl. .................................................... 556/440
[58] Field of Search ........................................ 556/440

[56] References Cited

U.S. PATENT DOCUMENTS

| 2,582,568 | 1/1952 | Speier | 556/440 |
| 2,956,044 | 10/1960 | Merker | 556/440 X |
| 3,258,477 | 6/1966 | Pluedermann et al. | 556/440 |
| 3,878,263 | 4/1975 | Martin | 556/440 X |
| 4,478,990 | 10/1986 | Koluo et al. | 556/440 X |
| 4,568,760 | 2/1986 | Sallenkenp et al. | 556/440 |
| 4,845,259 | 7/1989 | Arai et al. | 556/440 |
| 4,946,977 | 8/1990 | Bernhardt et al. | 556/440 |

Primary Examiner—Paul F. Shaver
Attorney, Agent, or Firm—Felfe & Lynch

[57] ABSTRACT

A quaternary pyridinium halide is used as the phase transfer catalyst in a process for the preparation of an organosilane containing methacryloyloxy or acryloyloxy groups by reacting an alkali metal methacrylate or alkali metal acrylate with a chloroalkylsilane.

3 Claims, No Drawings

PROCESS FOR THE PREPARATION OF ORGANOSILANES CONTAINING METHACRYLOYLOXY OR ACRYLOYLOXY GROUPS

FIELD OF THE INVENTION

This invention relates to a novel process for the preparation of organosilanes which contain methacryloyloxy or acryloyloxy groups. Such organosilanes are hereinafter referred to as "acryloylsilanes." The process is based on the known reaction of alkali metal methacrylates or alkali metal acrylates with chloroalkylsilanes in the presence of phase transfer catalysts.

BACKGROUND OF THE INVENTION

The reaction is disclosed in Japanese Patent Application 51348/65. It is there stated that acryloylsilanes of the formula

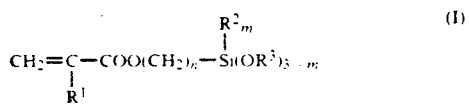

wherein $R^1$ is hydrogen or methyl, $R^2$ and $R^3$ are identical or different alkyls of 1 to 4 carbon atoms, m is 0, 1 or 2, and n is a whole number from 1 to 4, can be prepared by reacting a solid alkali metal salt of methacrylic acid or acrylic acid with a chloroalkylsilane of the formula

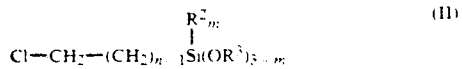

wherein $R^2$, $R^3$, m and n have the meanings previously defined, in the presence of a quaternary ammonium salt as a solid/liquid phase transfer catalyst.

The Japanese application mentions triethylamine, dimethylaniline, tetramethylammonium chloride and benzyltrimethylammonium chloride as suitable phase transfer catalysts. The two last-mentioned compounds are used as phase transfer catalysts in the Examples of the Japanese application for the reaction between the solid phase, consisting of the alkali metal salt of methacrylic or acrylic acid, and the liquid phase consisting of the chloroalkylsilane.

When these catalysts are used, high reaction temperatures of 140° to 180° C. are required, and the reaction time is in some cases up to 10 hours. Furthermore, a large excess of chloroalkylsilane, which may be up to 10 times the molar amount of alkali metal methacrylate or alkali metal acrylate is required. Moreover, solvents such as, for example, dimethyl-formamide, toluene or xylene must be used.

The yields of organosilane in this known process are substantially below 90% and frequently only 70%. With a molar ratio of alkali metal (meth)-acrylate/chloroalkylsilane of 1:1, the yield is actually only 65%, and large amounts of polymeric material are formed as a by-product. In addition, the large excess of chloroalkylsilane, the solvent, the long reaction time and the high reaction temperatures are decisive disadvantages. Long reaction times and a large excess of chlorosilane lead to a considerable reduction in the space-time yield. Moreover, the large excess of chloroalkylsilane and the use of a solvent have an adverse effect on the energy balance in the purification of the organosilane target product by distillation. The use of a solvent also has an adverse effect on the yield of organosilane.

High temperatures not only favor the formation of undesired polymeric by-products, but also lead to a virtually quantitative decomposition of the quaternary ammonium salt. Those skilled in the art are aware of the fact that quaternary salts decompose rapidly above 110° to 120° C. As a result of an anion exchange of halide for (meth)acrylate, silicon-free methacrylates or acrylates and tertiary amines are formed in the thermal decomposition of the quaternary ammonium salt. The decomposition products formed by trimethylbenzylammonium methacrylate or acrylate may be the corresponding high-boiling-point benzyl methacrylate or acrylate and dimethylbenzylamine, which can be separated from the acryloylsilane only with difficulty by distillation. Those skilled in the art know that these impurities may considerably interfere with, or even prevent, the use of the acryloylsilanes of the formula I above. Thus, the benzyl esters form oily films on aqueous solutions of the acryloylsilanes and prevent the use of such solutions as sizes for glass fibers. On the other hand, tertiary amines may adversely affect the use of the acryloylsilanes in peroxide-initiated polymerization reactions, since they may increase the polymerization rate in an undesirable manner.

OBJECTS OF THE INVENTION

It is therefore an object of the present invention to devise a method for performing the reaction between an alkali metal (meth)acrylate and a chloroalkylsilane to form an acryloylsilane in such a way that low reaction temperatures can be employed, a high space-yield is obtained, and the amount of polymeric reaction by-products, silicon-free methacrylates or acrylates and tertiary amines is as low as possible. Other objects and advantages of the present invention will become apparent as the description thereof proceeds.

DESCRIPTION OF THE INVENTION

We have discovered that the above object is achieved by a process for the preparation of an acryloylsilane of the formula

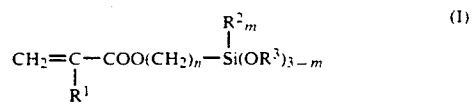

wherein $R^1$ is hydrogen or methyl,
$R^2$ is alkyl of 1 to 4 carbon atoms,
$R^3$ is alkyl of 1 to 4 carbon atoms or alkoxy alkyl of a total number of 2 to 4 carbon atoms,
m is 0, 1 or 2, and
n is 1, 3 or 4,
which comprises reacting an alkali metal salt of methacrylic acid or acrylic acid with an haloalkylsilane of the formula

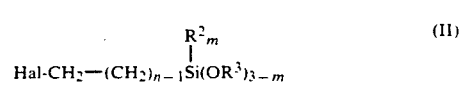

wherein $R^2$, $R^3$, m and n have the meanings previously defined, and Hal is chlorine or bromine, at a temperature of 80° to 150° C. in the presence of a phase transfer catalyst of the formula

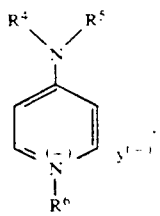

wherein Y is halogen,
$R^4$, $R^5$ and $R^6$, which may be identical to or different from each other, are each independently aliphatic radicals of 1 to 12 carbon atoms, cycloaliphatic radicals of 5 to 7 carbon atoms or benzyl,
$R^4$ and $R^5$ together with each other may be $(-CH_2-)_p$, where p is 4, 5 or 6, and the ring formed by $R^4$, $R^5$ and N may be interrupted by an oxygen atom between vicinal carbon atoms, and
$R^6$ may be an organosilyl radical of the formula

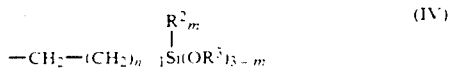

wherein $R^2$, $R^3$, m and n have the meanings previously defined.

In the process of the present invention it is possible to employ considerably lower temperatures than in the process described in the Japanese publication and nevertheless obtain yields which are far higher than in the known process. In particular, the amount of polymeric by-products, silicon-free methacrylates or acrylates and tertiary amines formed by the reaction is extremely low since the pyridinium salts used as phase transfer catalysts have a substantially higher thermal stability than the phase transfer catalysts based on quaternary ammonium salts heretofore used.

Examples of pyridinium salts of the formula III above which are suitable for use as phase transfer catalysts in the process according to the present invention are the following:

1-(2'-ethylhexyl)-4-dimethylaminopyridinium bromide,
1-(2'-ethylhexyl)-4-di-n-butylaminopyridinium chloride,
1-(2'-ethylhexyl)-4-di-n-hexylaminopyridinium chloride,
1-neopentyl-4-(4'-methylpiperidinyl)pyridinium chloride,
1-n-octyl-4-dimethylaminopyridinium bromide,
1-neopentyl-4-di-n-butylaminopyridinium chloride,
1-(2'-ethylhexyl)-4-(4'-methylpiperidinyl)pyridinium chloride,
1-(2'-ethylhexyl)-4-morpholinylpyridinium chloride,
1-(3'-trimethoxysilylpropyl)-4-dimethylaminopyridinium chloride,
1-(3'-triethoxysilylpropyl)-4-dimethylaminopyridinium chloride,
1-(3'-trimethoxysilylpropyl)-4-di-n-butylaminopyridinium chloride,
1-(3'-trimethoxysilylpropyl)-4-(4'-methylpiperidinyl)pyridinium chloride,
1-trimethoxysilylmethyl-4-di-n-hexylaminopyridinium chloride,
1-(4'-trimethoxysilylbutyl)-4-di-n-butylaminopyridinium chloride,
1-(3'-trimethoxysilylpropyl)-4-dicyclohexylaminopyridinium chloride or
1-(3'-triethoxysilylpropyl)-4-dibenzylaminopyridinium chloride.

Bis-salts, such as 1,10-bis-(4'-dihexylaminopyridinium)-decanoyl dibromide are also suitable.

1-(3'-Trimethoxysilylpropyl)-4-dimethylaminopyridinium chloride and 1-(3'-triethoxysilylpropyl)-4-dimethylaminopyridinium chloride are particularly suitable.

The pyridinium salts which are used as phase transfer catalysts pursuant to the present invention can be prepared in situ by heating a base pyridine together with some or all of the total required amount of haloalkylsilane before initiation of the reaction with the alkali metal salt of (meth)acrylic acid. Since the pyridinium salts of the formula III are used as phase transfer catalysts, the reaction rate of the reaction of an alkali metal salt of methacrylic acid or acrylic acid with an haloalkylsilane of the formula II is considerably increased compared with the known process, while at the same time the reaction temperature is reduced and the reaction time is decreased. Thus, the reaction temperature in the process of the present invention is 80° to 150° C., preferably 100° to 140° C., and the reaction time is between 15 and 180 minutes, preferably between 30 and 120 minutes.

The phase transfer catalyst is used in amounts of 0.001 mols to 0.05 mols, preferably in amounts of 0.005 mols to 0.03 mols, based on 1 mol of alkali metal methacrylate or acrylate.

The reactants are generally used in a stoichiometric ratio. A small excess of either haloalkylsilane or alkali metal (meth)acrylate may also be used, so that the molar ratio of alkali metal (meth)acrylate to haloalkylsilane should preferably be 1.2:1 to 1:1.2.

The reaction is preferably carried out in the absence of solvents. However, it is also possible to begin the reaction in the presence of an organic anhydrous solvent, such as an alcohol, which is introduced together with one of the reactants into the reaction system. Such a solvent should, however, then be substantially removed from the reaction mixture in the course of the reaction, preferably as early as the onset of the reaction.

By avoiding a large excess of haloalkylsilane and by dispensing with solvents in the reaction mixture, high spacetime yields as well as an advantageous energy balance are achieved, since there is no removal of unreacted chloroalkylsilane and of solvent by distillation. Compared with known processes, the process according to the present invention produces acryloylsilanes of high purity even without expensive column distillation of the reaction product.

In accordance with the present invention the alkali metal methacrylate or alkali metal acrylate reactant may be used in the form of its potassium or sodium salt. The reactants may be employed in the reaction both in solid form or in the form of a solution or dispersion in a suitable solvent. In a preferred embodiment, a methacrylate or acrylate produced by neutralization of methacrylic acid or acrylic acid with an alcoholic solution of potassium alcoholate or sodium alcoholate is used as the reactant. The solution or dispersion thus obtained is admixed with the haloalkylsilane and with the phase transfer catalyst, and the alcohol is then distilled off. The reaction between the alkali metal methacrylate or acrylate and the haloalkylsilane begins with the removal of the alcohol.

Examples of haloalkylsilanes of the formula II which can be used in the reaction of the present invention are the following:
chloromethyldimethylmethoxysilane,
3-chloropropyltrimethoxysilane,
3-chloropropyltriethoxysilane,
3-chloropropyltris(methoxyethoxy)silane,
3-chloropropylmethyldimethoxysilane,
3-chloropropylbutyldimethoxysilane,
4-chlorobutyltrimethoxysilane,
4-chlorobutylmethyldimethoxysilane or
4-chlorobutyltris(methoxyethoxy)silane.

The reaction of the alkali metal methacrylate or acrylate with the haloalkylsilane of the formula II is carried out by mixing the reactants and the phase transfer catalyst in the chosen molar ratio. The reaction mixture is then heated to the reaction temperature accompanied by constant thorough mixing. A solvent which may have been added is distilled off.

After the reaction has gone to completion, the acryloylsilane reaction product is isolated in conventional manner. Advantageously, it is distilled off, either after the precipitated alkali metal chloride has been separated or directly from the resulting reaction mixture. To protect the acryloylsilane reaction product, it is generally advantageous to perform the distillation under reduced pressure.

It is of advantage to add conventional polymerization inhibitors to the reaction mixture during the reaction. Examples of compounds which are suitable for this purpose are hydroquinone, hydroquinone monomethyl ether, N,N'-diphenyl-p-phenylene-diamine, phenyl-2-naphthylamine and 2,6-di-tert-butyl-4-methylphenol. They are added to the reaction mixture in amounts of 0.001 to 1% by weight, based on the amount of acryloylsilane. The polymerization inhibitors may be used individually or also in admixture with each other. The same inhibitors are also added to the distilled pure product or to the pure product isolated in another manner.

The acryloylsilanes of the formula I are useful, for example, as adhesion promoters in sizes for glass fibers.

The following Examples illustrate the present invention and will enable others skilled in the art to understand it more completely. It should be understood, however, that the invention is not limited solely to the particular Examples given below.

EXAMPLE 1

86 g (1 mol) of methacrylic acid was neutralized, while stirring, with 280 g of a 25% solution of potassium methylate in methanol. Thereafter, 0.6 g of N,N'-diphenyl-p-phenylenediamine, 2.8 g (0.009 mol) of 1-(2'-ethylhexyl)-4-dimethylaminopyridinium chloride and 198.5 g (1 mol) of 3-chloropropyltrimethoxysilane were added while continuously stirring, and the methanol was distilled off. The reaction mixture was maintained at 125° C. for 1.5 hours and, after cooling, it was separated from the precipitated potassium chloride by filtration. The potassium chloride was washed with methanol. The methanol was evaporated from the combined filtrates, and the residue was distilled under reduced pressure. 230 g of 3-methacryloxypropyltrimethoxysilane having a boiling of 82° C. (0.4 mbar) were obtained, which corresponds to a yield of 92.7% of theory, based on the amount of methacrylic acid used. The purity of the product was 98.5%. In the gas chromatogram only traces of 4-dimethylaminopyridine and 0.01% of 2-ethylhexyl methacrylate were detectable.

EXAMPLE 2

110.2 g (1 mol) of potassium acrylate were admixed with 198.5 g (1 mol) of 3-chloropropyltrimethoxysilane, 2.8 g (0.01 mol) of 1-neopentyl-4-(4'-methylpiperidinyl)-pyridinium chloride and 0.3 g of N,N'-diphenyl-p-phenylenediamine, and the mixture was heated to 128° C. while stirring. After 2 hours at this temperature, the reaction mixture was cooled and the potassium chloride which had precipitated was filtered off. The potassium chloride was washed with 50 g of methanol. The methanol was evaporated from the combined filtrates, and the residue was distilled under reduced pressure, whereby 217 g of 3-acryloxypropyltrimethoxysilane with a boiling point of 80° C. (0.5 mbar) were obtained. The yield was 92.7% of theory, based on the amount of potassium acrylate which was used. The purity of the product was 98.8%. In the gas chromatogram only traces of neopentyl acrylate and 4-(4'-methylpiperidinyl)pyridine were detectable.

EXAMPLE 3

54 g (0.5 mol) of sodium methacrylate were admixed with 99.3 g (0.5 mol) of 3-chloropropyltrimethoxysilane, 1.6 g (0.006 mol) of 1-(2'-ethylhexyl)-4-dimethylaminopyridinium chloride and 0.4 g of N,N'-diphenyl-p-phenylenediamine, and the mixture was heated at 120° C. for 1.5 hours, while stirring. The sodium chloride which precipitated as a by-product was filtered off and washed with 80 g of methanol. The methanol was evaporated from the combined filtrates, and the residue was distilled under reduced pressure, whereby 112 g of 3-methacryloxypropyltrimethoxysilane having a boiling point of 82° C. (0.4 mbar) were obtained. The yield was 90.3% of theory, based on the amount of sodium methacrylate used. The purity of the product was 98.5%. In the gas chromatogram only traces of 2-ethylhexyl methacrylate and 4-dimethylaminopyridine were detectable.

EXAMPLE 4

124 g (1 mol) of potassium methacrylate were admixed with 198.5 g (1 mol) of 3-chloropropyltrimethoxysilane, 2.7 g of 1-(3'-trimethoxysilylpropyl)-4-dimethylaminopyridinium chloride and 0.5 g of N,N'-diphenyl-p-phenylamine, and the mixture was heated to 135° C. while stirring. After 1 hour at this temperature the mixture was cooled and the potassium chloride which had precipitated was filtered off and washed with 60 g of methanol. The methanol was evaporated from the combined filtrates, and the residue was distilled under reduced pressure. 225 g of 3-methacryloxypropyltrimethoxysilane having a boiling point of 82° C. (0.4 mbar) were obtained. The yield was 90.7% of theory, based on the amount of potassium methacrylate which was used. The purity of the product was 99.0%. In the gas chromatogram only traces of 4-dimethylaminopyrrdine were detectable. A 2% solution of the product in water with a pH of 4 contained no oily separation of any kind.

EXAMPLES 5 TO 8

Example 4 was repeated, except that the chloroalkylsilanes and the phase transfer catalysts A to D shown in Table 1 below were used instead of 3-chloropropyltrimethoxysilane and 1-(3'-trimethoxysilylpropyl)-4- dimethylaminopyridinium chloride, respectively. The Table also shows the yields of the methacryloxysilanes which were obtained as well as their boiling points.

TABLE 1

| Example | Chloroalkylsilane [1 mol] | Phase transfer catalyst Designation | Mol | Methacryloyloxysilane | Yield g | Yield* % | Boiling point °C./mbar |
|---|---|---|---|---|---|---|---|
| 5 | 3-Chloropropyl-triethoxysilane | A | 0.009 | 3-Methacryloyloxy-propyltriethoxysilane | 268.2 | 92.3 | 92/0.25[1] |
| 6 | Chloromethyldi-methylmethoxy-silane | B | 0.006 | Methacryloyloxymethyl-dimethylmethoxysilane | 169.7 | 90.2 | 70/19.5[2] |
| 7 | 4-Chlorobutyl-trimethoxysilane | C | 0.01 | 4-Methacryloyloxy-butyltrimethoxysilane | 239.2 | 91.2 | 82/0.15[3] |
| 8 | 3-Chloropropyl-methyldimethoxy-silane | D | 0.015 | 3-Methacryloyloxy-propylmethyldimethoxy-silane | 216.9 | 93.3 | 66.5/0.25[4] |

*Based on potassium methacrylate used
A 1-(3-Triethoxysilylpropyl)-4-dimethylaminopyridinium chloride
B 1-Trimethoxysilylmethyl-4-di-n-hexylaminopyridinium chloride
C 1-(4-Trimethoxysilylbutyl)-4-di-n-butylaminopyridinium chloride
D 1-(3-Trimethoxysilylpropyl)-4-di-n-butylaminopyridinium chloride
[1-4]The distillates contain only traces of the base pyridines

EXAMPLE 9

1.74 g (0.015 mol) of 4-dimethylaminopyridine were dissolved in 201.5 (1.015 mol) of 3-chloropropyltrimethoxysilane, and the solution was heated to 135° C. while stirring, and was maintained at this temperature for 15 minutes. After the solution had been cooled to 60° C., 124.2 g (1 mol) of potassium methacrylate and 0.6 g of N,N'-diphenyl-p-phenylenediamine were added. The mixture was then heated to 135° C. again and maintained at that temperature for 1 hour. Thereafter, it was cooled, and the potassium chloride which had precipitated was filtered off and washed with 80 g of methanol. The methanol was evaporated from the combined filtrates, and the residue was distilled under reduced pressure. 228.1 g of 3-methacryloxypropyl-trimethoxysilane having a boiling point of 83° C. (0.4 mbar) were obtained. The yield was 92% of theory, based on the amount of potassium methacrylate used. The purity of the end product was 99.0%. In the gas chromatogram only traces of 4-dimethylaminopyridine were detectable.

COMPARATIVE EXAMPLE 10

Example 4 was repeated, except that instead of 1-(3'-trimethoxysilylpropyl)-4-dimethylaminopyridinium chloride, 3.0 g (0.016 mol) of trimethylbenzylammonium chloride were used as the phase transfer catalyst. After distillation of the filtrate under reduced pressure, 195 g of distillate with a boiling point of 60° to 86° C. (0.3 mbar) were obtained. Gas chromatographic analysis of the distillate indicated that it contained 35.0 g of 3-methacryloxypropyltrimethoxysilane, which corresponds to a yield of 14.1% of theory, based on the amount of potassium methacrylate which was used. The distillate contained 0.37% dimethylbenzylamine and 0.48% benzylmethacrylate. 28.5 g of 3-methacryloxy-propyltrimethoxysilane having a boiling point of 90° C. (1 mbar) were obtained by distillation on a packed column (packing material: Raschig rings) under reduced pressure. The purity of the product was 97.1%, as determined by gas chromatographic analysis. A 2% solution of the product in water with a pH of 4 exhibited a clearly visible oil film on the surface. After extraction with n-hexane, this film was identified to be a mixture of dimethylbenzylamine and benzyl methacrylate by mass spectroscopic analysis.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing an organosilane of the formula $$CH_2=C-COO(CH_2)_n-Si(OR^3)_{3-m}$$
$$\underset{R^1}{|} \quad \underset{}{|R^2_m}$$

wherein $R^1$ is hydrogen or methyl,
  $R^2$ is alkyl of 1 to 4 carbon atoms,
  $R^3$ is alkyl of 1 to 4 carbon atoms or alkoxyalkyl of a total number of 2 to 4 carbon atoms,
  m is 0, 1 or 2, and
  n is 1, 3 or 4, which comprises reacting an alkali metal methacrylate or alkali metal acrylate with an haloalkylsilane of the formula $$Hal-CH_2-(CH_2)_{n-1}Si(OR^3)_{3-m}$$
$$\underset{}{|R^2_m}$$

wherein $R^2$, $R^3$, m and n have the meanings previously defined, and Hal is chlorine or bromine, at a temperature of 80° to 150° C. in the presence of a pyridinium salt of the formula wherein Y is halogen $R^4$, $R^5$ and $R^6$, which may be identical to or different each other are independently aliphatic radicals of 1 to 12 carbon atoms, cycloaliphatic radicals of 5 to 7 carbon atoms or benzyl, or $R^4$ and $R^5$ together with each other may be $(-CH_2-)_p$, where p is 4, 5 or 6 and the ring formed by $R^4$, $R^5$ and the nitrogen atom to which they are attached may be interrupted by an oxygen atom between vicinal carbon atoms, or $R^6$ may be an organosilane radical of the formula $$-CH_2-(CH_2)_{n-1}Si(OR^3)_{3-m}R^2_m$$

wherein $R^2$, $R^3$, m and n have the meanings previously defined, as a phase transfer catalyst.

2. The method of claim 1, wherein said phase transfer catalyst is a 1-(3'-trialkoxysilylpropyl-4-dimethylaminopyridinium chloride.

3. The method of claim 1, wherein the molar ratio of alkali metal methacrylate or alkali metal acrylate to haloalkylsilane is 1.2:1 to 1:1.2.

* * * * *